(12) United States Patent
Boese et al.

(10) Patent No.: US 8,032,203 B2
(45) Date of Patent: Oct. 4, 2011

(54) METHOD AND MEDICAL IMAGING SYSTEM FOR ACQUISITION OF IMAGE DATA BY USING A PACEMAKER SIGNAL TO CONTROL THE IMAGING SYSTEM

(75) Inventors: Jan Boese, Eckental (DE); Andreas Meyer, Möhrendorf (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 901 days.

(21) Appl. No.: 11/900,834

(22) Filed: Sep. 13, 2007

(65) Prior Publication Data

US 2008/0064974 A1    Mar. 13, 2008

(30) Foreign Application Priority Data

Sep. 13, 2006    (DE) .......................... 10 2006 042 997

(51) Int. Cl.
*A61B 6/00*    (2006.01)
*A61N 1/05*    (2006.01)

(52) U.S. Cl. ............ 600/425; 600/427; 600/428; 607/9; 607/10

(58) Field of Classification Search .................. 600/407, 600/411, 424, 427, 439; 607/2, 9, 10, 27, 607/30, 33, 115–132
See application file for complete search history.

(56) References Cited

U.S. PATENT DOCUMENTS

| 6,148,095 | A | * | 11/2000 | Prause et al. .................. 382/131 |
| 2003/0109901 | A1 | | 6/2003 | Greatbatch |
| 2005/0070786 | A1 | | 3/2005 | Zeijlemaker et al. |
| 2005/0249327 | A1 | * | 11/2005 | Wink et al. ....................... 378/8 |

* cited by examiner

*Primary Examiner* — Parikha Mehta

(57) ABSTRACT

The invention relates to a method and a medical imaging system for acquisition of image data of the heart using a medical imaging procedure during an intervention on the heart, while the heart is stimulated by a pacing signal from an external heart pacemaker, the acquisition and/or reconstruction of the image data being controlled, in particular triggered, by the pacing signal.

18 Claims, 1 Drawing Sheet

METHOD AND MEDICAL IMAGING SYSTEM FOR ACQUISITION OF IMAGE DATA BY USING A PACEMAKER SIGNAL TO CONTROL THE IMAGING SYSTEM

CROSS REFERENCE TO RELATED APPLICATIONS

This application claims priority of German application No. 10 2006 042 997.4 filed Sep. 13, 2006, which is incorporated by reference herein in its entirety.

FIELD OF THE INVENTION

The invention relates to a method for acquisition of image data of a body part of a patient using a medical imaging procedure, and a corresponding medical imaging system.

BACKGROUND OF THE INVENTION

In cardiology image-controlled diagnostic or therapeutic inventions are often performed on the heart, for example catheter ablation, balloon dilation and the insertion of a stent. In ablation treatments the heart wall is selectively sclerosed at selected points in order to remove electrical short-circuit paths in the heart and tachycardias associated with them. In such interventions intracardial electrodes are generally first inserted into the heart, with which the heart is stimulated by an external pacemaker during the intervention. This is called "pacing" and serves to improve control of the activity of the heart during the intervention.

Such an intervention is usually performed using x-ray image control. Said x-ray images can for example be recorded using a C-arm x-ray device, it being possible for the image recording unit fixed to the C-arm to be swiveled around the patient at any angle, enabling realtime x-ray images, known as fluoroscopy images, to be recorded.

3D data records can also be recorded using a C-arm, with the C-arm rotating in what is known as a rotation pass through approximately 180° plus the fan angle of the C-arm around the patient and recording 50-500 projection images. These can be reconstructed to form a 3D data record.

Additionally an electroanatomical mapping system is also often used in a catheter ablation, one or more catheters being inserted into the relevant ventricle for the electrophysiological mapping of the heart wall. By mapping the heart wall with the electrodes a potential map of the heart wall is created. The exact determination of the position of the electrodes is performed for example with electromagnetic localization systems (for example with the CARTO® system from Biosense, Webster, Calif., USA). Here sensors are integrated into the medical instrument to detect electromagnetic field changes, while a electromagnetic field is constructed around the patient. In this way the position of the medical instrument can be determined.

Also known is intracardial or intravascular ultrasound imaging, in which an ultrasound head is introduced into a catheter tip.

It is additionally known in the prior art for a three-dimensional CT (computer tomography) or MR (magnetic resonance) data record to be acquired prior to an image-controlled intervention on the heart, e.g. for treating atrial flutter. This provides more anatomical details than the fluoroscopy images recorded during the intervention. These can therefore be superimposed with the anatomical 3D data record during the intervention, allowing the cardiologist to navigate using anatomical data in real time. Normally the 3D image data record is acquired 2-3 days before the actual intervention. As a result, significant imprecisions often arise, because e.g. the left atrium may change.

Another problem with imaging the heart in general is the motion of the beating heart. The problem can be solved by ECG triggering in many imaging procedures. In the case of a pre-operatively recorded 3D image data record it is important to trigger this in the same phase of motion of the heart, with the heart also being looked at during the intervention. This situation is complicated even further because patients often do not have a regular heartbeat.

SUMMARY OF THE INVENTION

The object of the invention is therefore to provide a method and an apparatus for more exact reproducible acquisition of image data of the beating heart.

The invention solves this problem with the features of the claims, with the acquisition and/or reconstruction of the image data recorded with the imaging procedure being controlled by the pacing signal of an external heart pacemaker. The imaging procedure, e.g. the x-ray system, is therefore not supported by the trigger signal indirectly obtained from the ECG system, but directly by the trigger signal from the pacemaker. This guarantees that the phases of motion of the heart (contraction phase, relaxation phase, etc.) occur in a fixed pattern. This also offers the advantage that the heart rate can be artificially increased and thus also the acquisition rate of e.g. x-ray images, in each case in the same heart phase. In this way the acquisition of the image data can be accelerated as required. In the case of ECG-triggered live fluoroscopy images these can be refreshed more frequently.

Both the acquisition and the reconstruction of the image data can be controlled, i.e. triggered, by the pacing signal. This can be done by recording large amounts of image data at the same time as the pacing signal is recorded, following which the image data recorded during a particular heart phase is collated and reconstructed to form a 3D image data record.

In a particularly preferred manner, several imaging procedures are controlled by the pacing signal from the external heart pacemaker, especially at least two of the following imaging procedures: a C-arm x-ray device, an electroanatomical mapping system and an ultrasound device. In the case of the C-arm x-ray device both the recording of fluoroscopy images and the acquisition of a 3D image data record can be controlled by the pacing signal. This has the advantage that the image data records acquired with the various procedures represent exactly the same heart phases and thus can be very well merged with one another, i.e. for example superimposed. Because the patient need not be relocated between the applications of the various imaging procedures, the coordinates systems of the various imaging procedures also correspond to one another, so that the items of image data need not be registered with one another first.

If necessary, the pacing signal can also be phase-shifted before it is used to trigger the imaging procedure. This is especially expedient if an image is to be acquired in the rest phase of the heart. The contraction of the heart in fact follows on directly from the pacing signal, so that imaging is expediently triggered shortly before or about 200 ms after the pacing signal.

The phase-shifting can be effected by a phase-shifter optionally disposed in a control unit of the imaging procedure, integrated into the external heart pacemaker or provided as a separate device. Especially preferred is integration into the external heart pacemaker, since the trigger signal sent to the imaging procedure can then not only be phase-shifted by a predetermined time (e.g. 150 ms) to the pacing signal, but also by a predetermined fraction of the period of the pacing signal, e.g. by 45° or 90°. Expressed in ms, the time shift then varies with the pacing frequency. The phase-shifted pacing signal can be emitted e.g. at a separate output of the external heart pacemaker.

According to a particularly preferred embodiment the method has the following steps: (a) acquisition of a series of 2D images of the body part of the patient in one or more rotation passes of a C-arm x-ray system, with simultaneous recording of the pacing signal from the external heart pacemaker; (b) assignment of the 2D images in the series of 2D images from the rotation pass(es) to one particular heart phase in each case based on the pacing signal; (c) reconstruction of the 2D images assigned to a particular heart phase to form a 3D image data record representing the body part in this heart phase; and (d) acquisition of further images of the body part in this heart phase, triggered by the pacing signal with the C-arm x-ray device or another medical imaging procedure. Steps (a) to (d) are preferably performed without relocating the patient. This embodiment thus shows an example in which 2D images acquired with a C-arm are controlled by the pacing system and reconstructed to form a 3D image data record. This is done by assigning the 2D images to a particular heart phase on the basis of the pacing signal. This allows the reconstruction of a 3D image data record which represents the body part in this particular heart phase.

In addition other images of the body part triggered by the pacing signal can also be acquired in this precise heart phase, e.g. fluoroscopy images of the C-arm. Alternatively other images can be recorded by any other medical imaging procedure, such as ultrasound, electroanatomical mapping or infrared imaging.

In an especially preferred manner the 3D image data record is then displayed, overlaid by the other images of the body part, e.g. by superimposition or by displays of the various images arranged side by side.

The inventive method also permits the reconstruction of several 3D image data records that represent the body part in several consecutive heart phases. As a result this can also be displayed dynamically. Any other images acquired with another medical imaging procedure can also be dynamically displayed in the same way, thereby creating a well synchronized 4D display of images of the heart using different imaging procedures.

Preferably the body part is the heart on which the intervention is undertaken. This is preferably a minimally invasive procedure, especially ablation treatment, balloon dilation or the insertion of a stent.

The invention is also directed at a medical imaging system suitable for acquisition of image data of a body part of a patient during a diagnostic or therapeutic intervention on the heart. This includes a C-arm x-ray device and an external heart pacemaker which stimulates the patient's heart during the intervention by means of a pacing signal. The system is characterized in that the C-arm x-ray device has an input for the pacing signal from the external heart pacemaker and that the acquisition of 2D fluoroscopy images and the acquisition and/or reconstruction of 3D image data can be controlled by the pacing signal from the external heart pacemaker. A computing unit is of course also preferably present to perform the reconstruction, controlled by the pacing signal.

In an especially preferred manner, other devices for other imaging procedures are present, such as an ultrasound device or an electroanatomical mapping system, which likewise have an input for the pacing signal from the external heart pacemaker. All procedures involved in the intervention and based on ECG triggering are preferably supported by the pacing signal.

Preferably the imaging system is suitable for carrying out the inventive method.

BRIEF DESCRIPTION OF THE DRAWINGS

The invention is now explained in more detail on the basis of exemplary embodiments with reference to the attached drawings, in which.

DETAILED DESCRIPTION OF THE INVENTION

Figure 1:
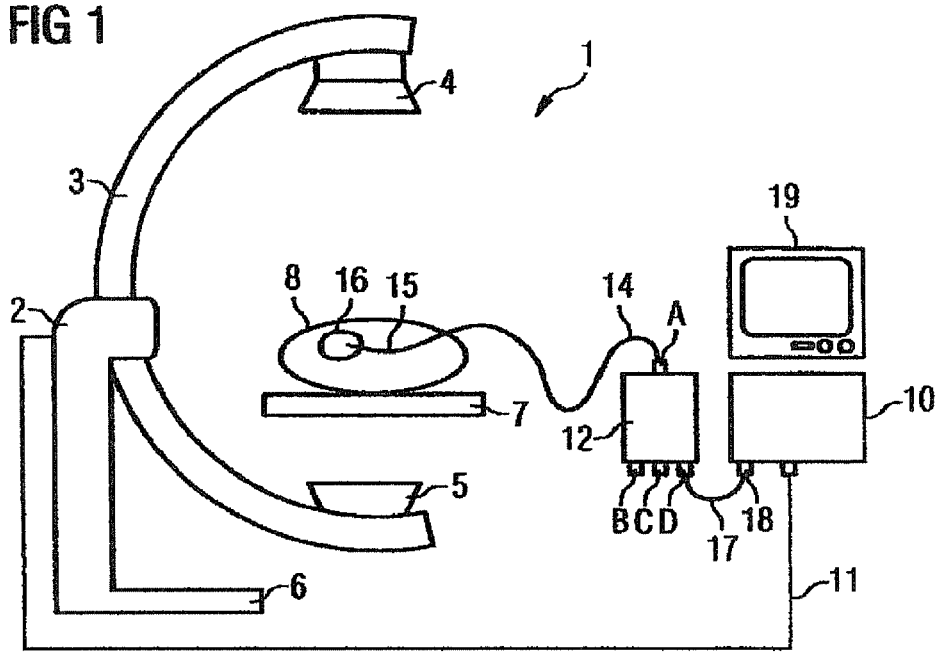
FIG. 1 shows a schematic cross-section through a C-arm x-ray system with an external heart pacemaker and FIG. 2 shows a schematic block diagram of an imaging system according to an embodiment of the invention.

With reference to FIG. 1, an imaging system 1 is shown there which includes a C-arm x-ray device 2. This has a C-arm 3, attached to the ends of which are an x-ray source 4 and an x-ray detector 5 respectively. The C-arm 3 is held by a stand 6 and can be swiveled, especially rotated, around a patient table 7. A patient 8 is shown on the table who is to undergo a cardiological intervention. Intracardial electrodes 15 are hence inserted into the heart 16, and are connected via a cable 14 to an external heart pacemaker 12. This has outputs A, B, C and D, at which in each case the pacing signal is emitted. Output D is connected via a cable 17 to the input 18 of a control apparatus 10 of the C-arm x-ray device 2. The control unit 10 contains in particular a processor and data memory and is used to control the movements, image recording and reconstructions of the C-arm device 2. To this end it is connected to the C-arm device 2 via signal lines 11. The images are displayed for the operator on a monitor 19.

The control unit 10 thus contains the pacing signal of the external heart pacemaker 12 and can control the C-arm accordingly. In particular it can establish, on the basis of the known delay times between electrical stimulation of the heart and contraction, at which times x-ray images are recorded within the heart cycle. For example, triggering is possible in each case at a particular moment in the heart cycle.

In order then to increase the trigger frequency, the operator can if necessary raise the heart frequency at the external heart pacemaker 12, so that more images can then be acquired per time unit.

Other imaging procedures, e.g. ultrasound or an electroanatomical mapping system, can be connected at the outputs B and C of the external heart pacemaker and can be supported by the pacing signal.

Figure 2:
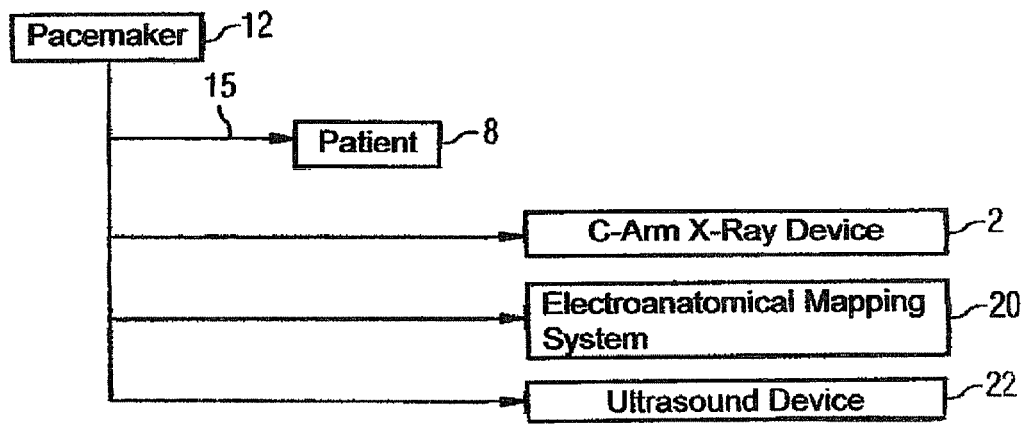

FIG. 2 shows the apparatus in FIG. 1 as a block diagram. Intracardial electrodes 15 run from the heart pacemaker 12 to the patient 8. In addition the pacing signal is however also branched and transmitted to three different imaging procedures 2, 20 and 22. The C-arm x-ray system is equipped with facilities for pacemaker-triggered 3D image reconstruction and 2D acquisition. The reference character 20 designates an electroanatomical mapping system as described above. An intracardial ultrasound system is provided at 22.

A particular application of the inventive method for using the pacing signal to start x-ray imaging is explained in the following:

A method is known for reducing the amount of contrast agent in cardiological interventions, in which in a first step a time-triggered series of images (also called a scene) is recorded with a high x-ray dosage after contrast agent has been administered. The anatomy can therefore be identified with high contrast and on a time-triggered basis on these images. In subsequent steps only fluoroscopy images without contrast agent being administered and with a low x-ray dosage are recorded, which are solely used to visualize the instrument inserted (e.g. a stent or catheter). These two series of images can in principle, based on the simultaneously recorded ECG signal, be superimposed on a synchronized basis on heart phases. However, in line with the principle disclosed in this document, the scenes cannot be exactly superimposed because of the variability of the heartbeat.

This problem is solved by the present invention: by using the pacing signal from the heart pacemaker as a trigger to start the x-ray imaging for each heart cycle it is guaranteed that the high-dosage scene can be superimposed precisely by the low-dosage scene. In this way a "cardiological roadmapping" can be performed.

With the help of the invention it essentially becomes easier to reproduce the merging of images from different medical imaging procedures or recording timepoints. The invention thus permits a 4D display of the merged 2D x-ray images with the 3D reconstruction of the heart.

The invention claimed is:

1. A method for acquiring an image data of a body part of a patient using a medical imaging system during an intervention on a heart of the patient, comprising:
    stimulating the heart during the intervention by a first pacing signal from an external heart pacemaker;
    controlling the imaging system by the first pacing signal;
    acquiring the image data using the imaging system for monitoring the intervention wherein a frequency of the first pacing signal is sufficient to meet a requirement of the image data acquisition;
    stimulating the heart during the intervention by a second pacing signal from the external heart pacemaker;
    controlling the imaging system by the second pacing signal; and
    acquiring image data using the imaging system for monitoring the intervention wherein a frequency of the second pacing signal is greater than the frequency of the first pacing signal to provide an increased image data acquisition rate.

2. The method as claimed in claim 1, wherein the medical imaging system is selected from the group consisting of: a C-arm x-ray device, an electroanatomical mapping system, and an ultrasound device.

3. The method as claimed in claim 2, wherein the medical imaging system is a C-arm x-ray device and further comprising:
    acquiring a series of a plurality of 2D images of the body part of the patient in one or more rotation passes of the C-arm x-ray device and simultaneously recording the pacing signal,
    assigning 2D images from the series to a particular heart phase based on the pacing signal, and
    reconstructing a 3D image data record in the particular heart phase from the 2D images assigned to the particular heart phase.

4. The method as claimed in claim 3, further comprising:
    acquiring a further image of the body part of the patient in the particular heart phase triggered by the pacing signal,
    superimposing the 3D image data record with the further image, and
    displaying the superimposed 3D image data record.

5. The method as claimed in claim 4, wherein the further image is selected from the group consisting of: 2D x-ray images acquired by the C-arm x-ray device, electroanatomical images acquired by the electroanatomical mapping system, and ultrasound images acquired by the ultrasound device.

6. The method as claimed in claim 3, wherein a plurality of 3D image data records are reconstructed in a plurality of heart phases and dynamically displayed and superimposed with other further images acquired in identical heart phases.

7. The method as claimed in claim 1, wherein the intervention is a minimally invasive procedure.

8. The method as claimed in claim 7, wherein the invasive procedure is selected from the group consisting of: an ablation treatment, a balloon dilation, and a stent insertion.

9. The method as claimed in claim 1, wherein the body part of the patient is the heart of the patient.

10. A medical imaging system for acquiring an image data of a body part of a patient during an intervention on a heart of the patient, comprising:
    an external heart pacemaker that generates a first and second pacing signals and stimulates the heart of the patient during the intervention by the first and second pacing signals; and
    a medical image device that acquires the image data based on the first and second pacing signals wherein a frequency of the first pacing signal is sufficient to meet a requirement of the image data acquisition and wherein a frequency of the second pacing signal is greater than the frequency of the first pacing signal to provide an increased data acquisition rate for providing more frequent refreshment of live images.

11. The medical image system as claimed in claim 10, wherein the medical imaging system is selected from the group consisting of: a C-arm x-ray device, an electroanatomical mapping system, and an ultrasound device.

12. The medical image system as claimed in claim 11, wherein the C-arm x-ray device:
    acquires a series of a plurality of 2D images of the body part of the patient in one or more rotation passes of the C-arm x-ray device and simultaneously records the pacing signal,
    assigns 2D images from the series to a particular heart phase based on the pacing signal, and
    reconstructs a 3D image data record in the particular heart phase from the 2D images assigned to the particular heart phase.

13. The medical image system as claimed in claim 12, wherein:
    a further image of the body part of the patient is acquired in the particular heart phase triggered by the pacing signal,
    the 3D image data record is superimposed with the further image, and
    the superimposed 3D image data record is displayed.

14. The medical image system as claimed in claim 13, wherein the further image is selected from the group consisting of: 2D x-ray images acquired by the C-arm x-ray device, electroanatomical images acquired by the electroanatomical mapping system, and ultrasound images acquired by the ultrasound device.

15. The medical image system as claimed in claim 12, wherein a plurality of 3D image data records are reconstructed in a plurality of heart phases and dynamically displayed and superimposed with other further images acquired in identical heart phases.

16. The medical image system as claimed in claim 10, wherein the intervention is a minimally invasive procedure.

17. The medical image system as claimed in claim 16, wherein the invasive procedure is selected from the group consisting of: an ablation treatment, a balloon dilation, and a stent insertion.

18. The medical image system as claimed in claim 10, wherein the body part of the patient is the heart of the patient.

* * * * *